United States Patent
Yadlowsky et al.

(10) Patent No.: US 9,730,576 B2
(45) Date of Patent: Aug. 15, 2017

(54) ENDOILLUMINATION USING DECENTERED FIBER LAUNCH

(75) Inventors: Michael J. Yadlowsky, Sunnyvale, CA (US); Michael Papac, North Tustin, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 545 days.

(21) Appl. No.: 13/571,074

(22) Filed: Aug. 9, 2012

(65) Prior Publication Data

US 2013/0041233 A1 Feb. 14, 2013

Related U.S. Application Data

(60) Provisional application No. 61/521,450, filed on Aug. 9, 2011.

(51) Int. Cl.
| | |
|---|---|
| *F21V 5/00* | (2015.01) |
| *A61B 1/07* | (2006.01) |
| *A61B 3/00* | (2006.01) |
| *G02B 6/42* | (2006.01) |
| *A61B 90/30* | (2016.01) |
| *A61B 1/00* | (2006.01) |
| *G02B 6/36* | (2006.01) |

(52) U.S. Cl.
CPC .............. *A61B 1/07* (2013.01); *A61B 3/0008* (2013.01); *A61B 90/30* (2016.02); *G02B 6/4206* (2013.01); *A61B 1/0017* (2013.01); *A61B 2090/306* (2016.02); *F04C 2270/041* (2013.01); *G02B 6/3624* (2013.01)

(58) Field of Classification Search
USPC ................. 362/551–582; 600/108, 248–249
See application file for complete search history.

(56) References Cited

U.S. PATENT DOCUMENTS

| | | | |
|---|---|---|---|
| 4,870,952 A | * | 10/1989 | Martinez ...................... 362/572 |
| 5,283,718 A | | 2/1994 | Stephenson et al. |
| 6,478,478 B1 | | 11/2002 | Campbell |

(Continued)

FOREIGN PATENT DOCUMENTS

| | | |
|---|---|---|
| EP | 1039321 A2 | 9/2000 |
| JP | 2002231008 A | 8/2002 |
| WO | 2005067573 A2 | 7/2005 |

OTHER PUBLICATIONS

International Search Report, PCT/US2012/050180, International Searching Authority, Oct. 16, 2012, 2 pgs.

(Continued)

*Primary Examiner* — Sean Gramling

(57) ABSTRACT

An endoilluminator system includes an endoilluminator probe and an illumination source. The endoilluminator probe includes a nano-scale optical fiber and a probe fiber connector, and the illumination source includes a source fiber connector. The illumination source is configured to produce an illumination spot at the source fiber connector having a diameter smaller than a diameter of a fiber core of the nano-scale optical fiber. The probe fiber connector and the source connector are configured when connected to align the illumination spot off-center relative to the nano-scale optical fiber such that the angular distribution of light emitted by the nano-scale optical fiber is increased relative to aligning the illumination spot at a center of the nano-scale optical fiber.

6 Claims, 3 Drawing Sheets

(56) References Cited

U.S. PATENT DOCUMENTS

| | | | |
|---|---|---|---|
| 7,231,114 B2 * | 6/2007 | Jenkins et al. | 385/31 |
| 2002/0149924 A1 | 10/2002 | Falicoff et al. | |
| 2005/0152643 A1 | 7/2005 | Blauvelt et al. | |
| 2005/0259916 A1 | 11/2005 | Jenkins et al. | |
| 2006/0285796 A1 | 12/2006 | Cheng | |
| 2009/0227993 A1 | 9/2009 | Tang | |
| 2009/0232438 A1 * | 9/2009 | Shimotsu | G02B 6/262 |
| | | | 385/1 |
| 2011/0015528 A1 | 1/2011 | Kobayashi | |
| 2011/0085348 A1 | 4/2011 | Dobson | |
| 2011/0112377 A1 | 5/2011 | Papac et al. | |

OTHER PUBLICATIONS

Written Opinion, PCT/US2012/050180, International Searching Authority, Oct. 16, 2012, 5 pgs.

* cited by examiner

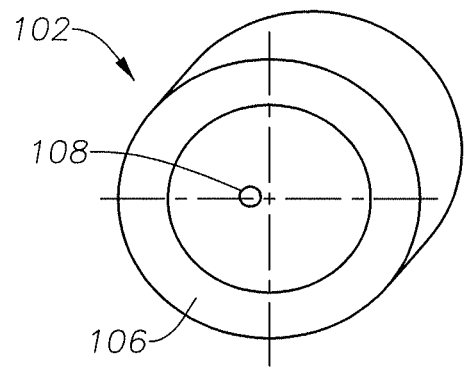
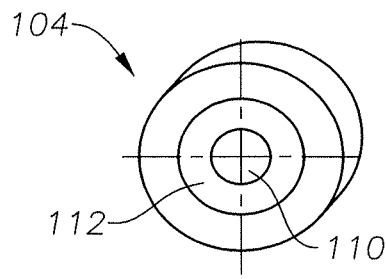
Fig. 2A    Fig. 2B
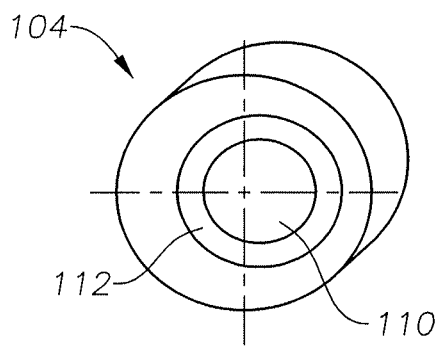
Fig. 3A
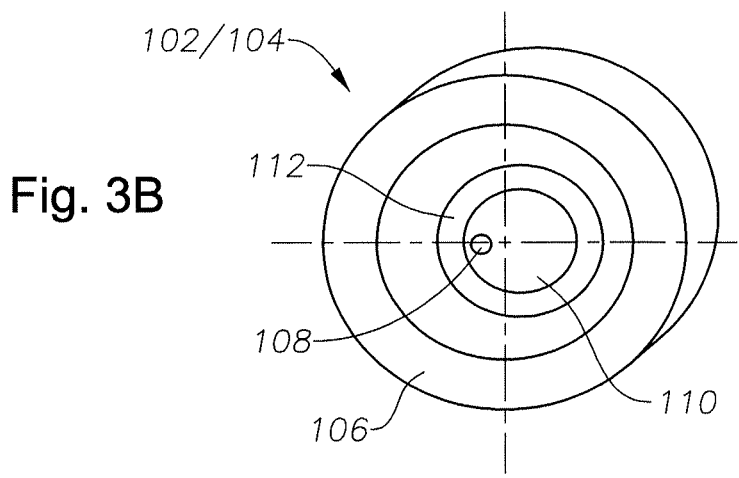
Fig. 3B

ENDOILLUMINATION USING DECENTERED FIBER LAUNCH

RELATED APPLICATIONS

This application claims priority to U.S. provisional application Ser. No. 61/521,450, filed on Aug. 9, 2011, the contents which are incorporated herein by reference.

BACKGROUND

1. Field of the Invention

Embodiments described herein relate to the field of microsurgical probes. More particularly, embodiments described herein are related to the field of endoillumination using decentered fiber launch.

2. Description of Related Art

The field of microsurgical procedures is evolving rapidly. Typically, these procedures involve the use of probes that are capable of reaching the tissue that is being treated or diagnosed. Such procedures make use of endoscopic surgical instruments having a probe coupled to a controller device in a remote console. Current state of the art probes are quite complex in operation, often times requiring moving parts that are operated using complex mechanical systems. In many cases, an electrical motor is included in the design of the probe. Most of the prior art devices have a cost that makes them difficult to discard after one or only a few surgical procedures. Furthermore, the complexity of prior art devices leads generally to probes having cross sections of several millimeters. These probes are of little practical use for ophthalmic microsurgical techniques. In ophthalmic surgery, dimensions of one (1) mm or less are preferred, to access areas typically involved without damaging unrelated tissue.

Because of the relatively small aperture, endoilluminators for the interior of the eye face additional challenges. First, the endoilluminator must couple efficiently to the probe to provide enough light energy to reach the interior of the eye. Second, because the probe tip is so small, the light must be able to spread over a wide solid angle to illuminate the surgical field (ideally corresponding to an in-plane angle of seventy degrees or greater). Both of these considerations have made it difficult to produce small gauge endoilluminators.

SUMMARY

According to particular embodiments of the present invention, an endoilluminator system includes an endoilluminator probe and an illumination source. The endoilluminator probe includes a nano-scale optical fiber and a probe fiber connector, and the illumination source includes a source fiber connector. The illumination source is configured to produce an illumination spot at the source fiber connector having a diameter smaller than a diameter of a fiber core of the nano-scale optical fiber. The probe fiber connector and the source connector are configured when connected to align the illumination spot off-center relative to the nano-scale optical fiber such that the angular distribution of light emitted by the nano-scale optical fiber is increased relative to aligning the illumination spot at a center of the nano-scale optical fiber.

These and other embodiments of the present invention will be described in further detail below with reference to the following drawings.

BRIEF DESCRIPTION OF THE DRAWINGS

FIGS. 2A and 2B illustrate end views of complementary fiber connectors according to a particular embodiment of the present invention;

FIGS. 3A and 3B illustrate end views of complementary fiber connectors according to an alternative embodiment of the present invention;

In the figures, elements having the same reference number have the same or similar functions.

DETAILED DESCRIPTION

Various embodiments of the present invention provide a fiber connector system with a decentered launch of light beams into the probe optical fiber. Certain embodiments include a source fiber connector and a probe fiber connector, wherein an illumination spot emitted from the source fiber connector is offset from a center of the probe fiber. For example, the connectors can hold the central axes of the source emitter and the probe fiber offset relative to one another. In another example, the source emitter can be configured to emit an illumination spot off center relative to the probe fiber. Additional features of various embodiments of the present invention are described in the following explanation of the FIGs.

Various embodiments of the present invention provide improve endoillumination by increasing the angular distribution of the illuminated area using a decentered launch while providing equivalent or greater coupling efficiency for the illumination source to the probe. Previous systems have centered the illumination spot on the probe fiber in order to avoid significant drops in coupling efficiency, therefore making less light available for illumination. However, when using sufficiently small illumination spots and, in particular, when using illumination spots that can be decentered and still fall within the fiber cross-section, the spot can be decentered without significant illumination loss. The decentration does, however, significantly increase the angular distribution of the illumination, thus allowing a wider area to be illuminated with substantially equal brightness.

In previous systems, particularly xenon lamp assemblies, the illumination spot produced by the illumination source can be relatively large, meaning that decentering the spot produces significantly less illumination. By contrast, when illuminator systems using a tightly focused spot according to various embodiments of the present invention are used, decentration can be exploited for a larger angular distribution without such losses. Thus, various embodiments of the present invention may be particularly useful for illumination sources that produce tightly focused illumination spots, such as supercontinuum lasers.

Figure 1:
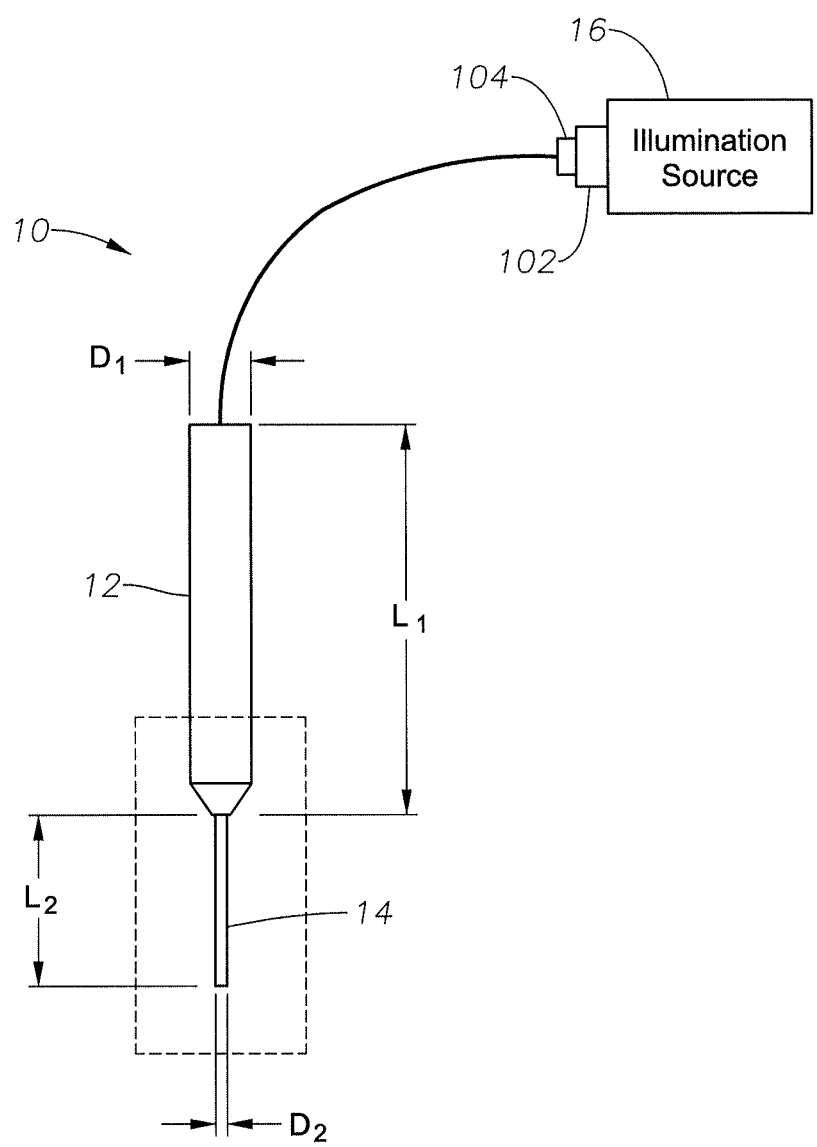
FIG. 1 shows a schematic of an ophthalmic endoilluminator system according to a particular embodiment of the present invention.

In general, the following description relates to ophthalmic surgical endoprobes including a handle suitable for being held in one hand and a cannula that is at least partially rigid that is suitable for insertion into a small incision. Such a system is schematically illustrated in FIG. 1, which includes an endoprobe 10 with a handle 12 having a length L1 suitable for being held in a single hand and cannula 14 having a diameter D and length L2. The endoprobe 10 is optically coupled to an illumination source 16 by a probe fiber connector 104 connected to a source fiber connector 102. The diameter D of the cannula 14 is typically measured in according to the gauge system for needles and similar medical devices; for ophthalmic applications, this is typically 20 Ga (0.84 mm) or less. While the discussion relates to ophthalmic endoilluminators, it could also apply to similar endoillumination devices that are inserted through small incisions to produce wide-angle illumination. For purposes of this specification, "small gauge" will be used to refer to endoilluminators of 20 Ga diameter or less, and "nano-scale" will be used to refer to optical fibers having an outer diameter of 100 µm or less.

FIGS. 2A and 2B illustrate end views of complementary fiber connectors 102 and 104 according to a particular embodiment of the present invention. In the depicted embodiment, the source connector 102 includes a bulkhead 106 for holding a probe fiber connector 104 in alignment with the illumination spot 108 produced by the illumination source 20. The location of the illumination spot 108 is focused off-center relative to the bulkhead 106, so that when the probe fiber connector 104 is centered by the bulkhead, the illumination spot 108 will enter a fiber core 110 of a probe optical fiber (including core 110 and cladding 112) decentered.

An alternative embodiment is illustrated in FIGS. 3A and 3B. In FIGS. 3A and 3B, the probe fiber is positioned off-center in the probe fiber connector 104. When the probe fiber connector 104 is inserted into the bulkhead, it is automatically aligned so that a centered illumination spot 108 from the illumination source 20 will be off-center relative to the fiber core 110 of the probe fiber, as shown in FIG. 4B. Thus, the alignment of the source fiber connector 102 and the probe fiber connector 104 produces a decentered launch of illumination light into the probe fiber.

Figure 4:
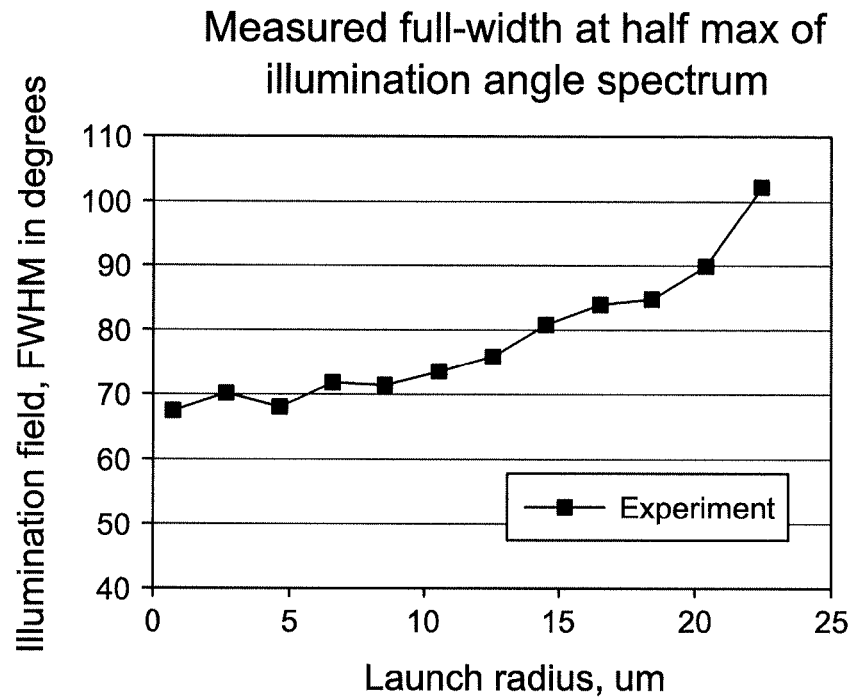
FIG. 4 is a graph illustrating the in-plane illumination angle corresponding to full-width at half maximum intensity for various amounts of decentration for a probe according to a particular embodiment of the present invention.

FIG. 4 illustrates the in-plane angular distribution to full-width at half maximum (FWHM) of light intensity as measured from an example probe fiber into which an illumination spot is aligned for a decentered launch into the fiber. For purposes of this specification, light emitted from an endoilluminator will be considered as having an "angular distribution" of a certain angle if the in-plane angular distribution to FWHM spans that angle. In the example provided, the illumination spot size is about 1 µm into a fiber having a numerical aperture of 0.22. The plot illustrates that for decentration of up to 20 µm, the angular distribution out to which the FWHM extends rises from about 70 degrees to nearly 90 degrees.

Figure 5:
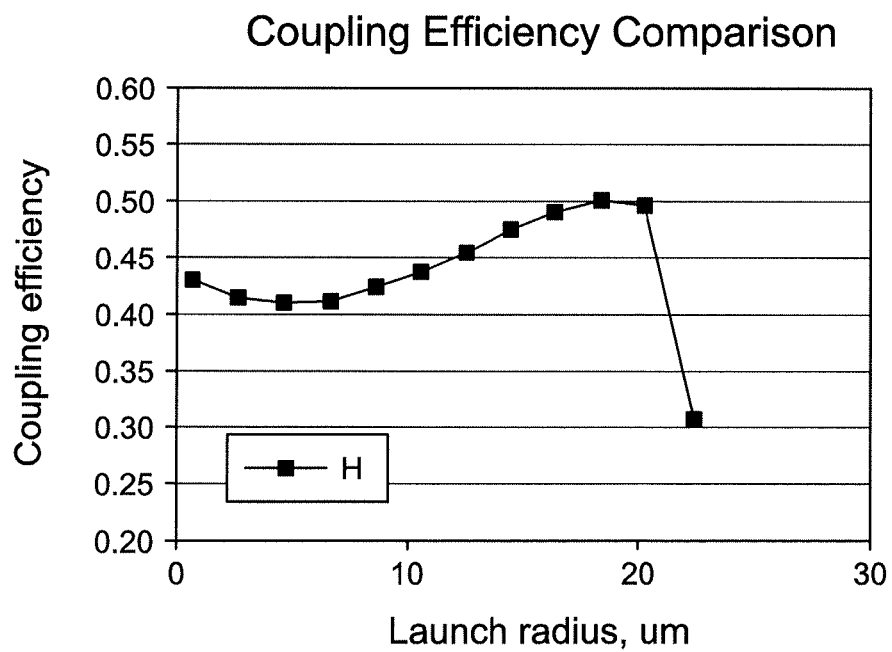
FIG. 5 is a graph illustrating coupling efficiency for various amounts of decentration for a probe according to a particular embodiment of the present invention.

FIG. 5 illustrates the coupling efficiency for the same optical fiber as a function of decentration. As shown in the plot of FIG. 5, decentration of the illumination spot coupled into the fiber can actually increase slightly as long as the illumination spot still falls onto the fiber core, falling off only when the spot moves off of the fiber core. Given the higher coupling efficiency and angular distribution, the decentered alignment of the endoilluminator system may provide a larger angular distribution without even needing to make the relatively minor tradeoff between brightness and angular intensity.

Various embodiments of the present invention provide an endoilluminator system including fiber connectors providing a decentered alignment between an illumination spot and a probe optical fiber. Embodiments of the invention described above are exemplary only. One skilled in the art may recognize various alternative embodiments from those specifically disclosed. Those alternative embodiments are also intended to be within the scope of this disclosure. As such, the invention is limited only by the following claims.

What is claimed is:

1. An endoilluminator system, comprising:
   an endoilluminator probe comprising:
      a cannula;
      a nano-scale optical fiber extending at least partially through the cannula and configured to emit light from a distal end of the cannula; and
      a probe fiber connector;
   an illumination source comprising a source fiber connector, the illumination source configured to produce an illumination spot at the source fiber connector, the illumination spot having a diameter equal to or less than 1 µm, the diameter of the illumination spot being smaller than a diameter of a fiber core of the nano-scale optical fiber, wherein the probe fiber connector and the source connector are configured when connected to align the center of the illumination spot off-center relative to the center of the nano-scale optical fiber such that the angular distribution of light emitted by the nano-scale optical fiber is increased relative to aligning the center of the illumination spot with the center of the nano-scale optical fiber, the center of the illumination spot being spaced from the center of the fiber core by a distance in the range of 5 µm to 20 µm.

2. The endoilluminator system of claim 1, wherein the distance between the center of the illumination spot and the center of the fiber core is at least 10 percent of the diameter of the fiber core of the nano-scale optical fiber.

3. The endoilluminator system of claim 1, wherein the illumination source is a supercontinuum laser.

4. The endoilluminator system of claim 1, wherein the nano-scale optical fiber is aligned off-center within the probe fiber connector.

5. The endoilluminator system of claim 1, wherein the illumination spot is produced at the source fiber connector off-center relative to a bulkhead of the source fiber connector.

6. The endoilluminator system of claim 1, wherein an angular distribution of the endoilluminator probe is at least eighty degrees.

* * * * *